US011963798B2

(12) United States Patent
Howard et al.

(10) Patent No.: US 11,963,798 B2
(45) Date of Patent: Apr. 23, 2024

(54) OPTICAL FORCE SENSOR WITH A CATHETER/SHEATH

(71) Applicant: Medtronic, Inc., Minneapolis, MN (US)

(72) Inventors: Stephen Howard, Forest Lake, MN (US); Carl Schu, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1059 days.

(21) Appl. No.: 16/683,890

(22) Filed: Nov. 14, 2019

(65) Prior Publication Data

US 2021/0145365 A1    May 20, 2021

(51) Int. Cl.
*A61B 5/00* (2006.01)
*A61B 18/02* (2006.01)
(Continued)

(52) U.S. Cl.
CPC .......... *A61B 5/6885* (2013.01); *A61B 5/6853* (2013.01); *A61B 18/02* (2013.01); *G01L 1/246* (2013.01); *A61B 2018/0212* (2013.01); *A61B 2090/064* (2016.02); *A61M 2025/0024* (2013.01)

(58) Field of Classification Search
CPC .... A61B 2034/2061; A61B 2018/2255; A61B 2562/0233; A61B 2562/0238; A61B 2018/00066; A61B 2018/00061; A61B 2018/00057
See application file for complete search history.

(56) References Cited

U.S. PATENT DOCUMENTS 8,075,498 B2    12/2011    Leo et al.
8,567,265 B2    10/2013    Aeby et al.
(Continued)

FOREIGN PATENT DOCUMENTS

WO    2019211112 A1    11/2019

OTHER PUBLICATIONS

International Search Report and Written Opinion dated Feb. 9, 2021, for corresponding International Application No. PCT/US2020/059005; International Filing Date: Nov. 5, 2020 consisting of 14-pages.

*Primary Examiner* — Ronald Hupczey, Jr.
(74) *Attorney, Agent, or Firm* — Michael Best & Friedrich LLP

(57) ABSTRACT

Devices, systems, and methods for quantifying applied pressure by a device against an area of tissue. In particular, the present technology is related to medical devices including an optical element with a fiber Bragg grating, systems including the medical devices, and methods of quantifying applied pressure by the medical device. In one embodiment, a medical device comprises an elongate body including a distal portion and a proximal portion opposite the distal portion, and an optical element located at the distal portion of the elongate body. In one embodiment, the optical element include an optical fiber with a fiber Bragg grating. In one embodiment, the medical device is part of a medical system comprising a control unit in communication with the medical device, the control unit including an optical interrogator in communication with the optical element and processing circuitry configured to receive data from the optical interrogator.

12 Claims, 12 Drawing Sheets

(51) Int. Cl.
  *A61B 90/00*    (2016.01)
  *A61M 25/00*    (2006.01)
  *G01L 1/24*     (2006.01)

(56) References Cited

U.S. PATENT DOCUMENTS

| | | |
|---|---|---|
| 8,622,935 B1 | 1/2014 | Leo |
| 2006/0200049 A1* | 9/2006 | Leo ................... A61B 5/065 |
| | | 600/587 |
| 2008/0218770 A1 | 9/2008 | Moll et al. |
| 2009/0076476 A1* | 3/2009 | Barbagli ............. A61B 5/283 |
| | | 600/587 |
| 2009/0099551 A1 | 4/2009 | Tung et al. |
| 2010/0069733 A1 | 3/2010 | Kastelein et al. |
| 2011/0087112 A1 | 4/2011 | Giovanni et al. |
| 2013/0090530 A1 | 4/2013 | Ramamurthy et al. |
| 2013/0253490 A1 | 9/2013 | Bitzer et al. |
| 2014/0336637 A1* | 11/2014 | Agrawal ............. A61B 5/6847 |
| | | 606/41 |
| 2015/0258270 A1 | 9/2015 | Kunis |
| 2015/0265334 A1* | 9/2015 | Franke .............. A61B 18/1492 |
| | | 606/34 |
| 2017/0105780 A1 | 4/2017 | Sara |

* cited by examiner

OPTICAL FORCE SENSOR WITH A CATHETER/SHEATH

CROSS-REFERENCE TO RELATED APPLICATION n/a

FIELD

The present technology is generally related to devices, systems, and methods for quantifying applied pressure by a device against an area of tissue. In particular, the present technology is related to medical devices including an optical element with a fiber Bragg grating, systems including the medical devices, and methods of quantifying applied pressure by the medical device.

BACKGROUND

Many medical procedures using minimally invasive medical devices, such as procedures performed within the heart, require at least a portion of the medical device to be pressed against an area of tissue. For example, transseptal puncture may be required to access the left atrium, and this puncture may be made by pressing a dilator, sheath, or other device against the septum and then advancing a puncture element (for example, a needle, trocar, guidewire, or the like) through the septum. Likewise, pulmonary vein occlusion by a balloon of a medical device requires the balloon to be pressed with sufficient force against the pulmonary vein ostium to prevent the flow of blood around the balloon and into the left atrium.

However, the amount of force exerted against various parts of the cardiac anatomy during a medical procedure is difficult to quantify with any reliable accuracy. For example, practitioners such as electrophysiologists, cardiologists, and/or surgeons may use ambiguous statements to explain how hard they are pushing against an area of tissue, which is nearly impossible to quantify. Further, such benchmarks are of little use for surgical training and education. This becomes even more difficult when the tissue being pushed against is of a larger area such as a catheter having a multi-electrode array or large-area devices or delivery tools.

Further, it is often difficult to precisely locate an area of target tissue, such as the fossa ovalis in the septum or a pulmonary vein ostium. Accordingly, angiographic techniques have been devised to ameliorate such drawbacks. For example, transesophageal and transthoracic echocardiography, intravascular ultrasound, and intracardiac echocardiography have all been used to determine the optimal transseptal puncture site. However, such methods may not be sufficient to locate the thin wall of the fossa ovalis, may present risks of patient injury and esophageal bleeding, and may result in longer procedure times and additional cost.

SUMMARY

The techniques of this disclosure generally relate to devices, systems, and methods for quantifying applied pressure by a device against an area of tissue. In particular, the present technology is related to medical devices including an optical element with a fiber Bragg grating, systems including the medical devices, and methods of quantifying applied pressure by the medical device. In one embodiment, a medical device comprises: an elongate body including a distal portion and a proximal portion opposite the distal portion; and an optical element located at the distal portion of the elongate body.

In one aspect of the embodiment, the optical element includes: at least one optical fiber having a distal portion and a proximal portion opposite the distal portion; and a fiber Bragg grating (FBG) located within the distal portion of the optical fiber.

In one aspect of the embodiment, the medical device is a dilator, wherein the medical device includes a lumen that is sized and configured to receive a puncture element.

In one aspect of the embodiment, the optical element is integrated with an external surface of the elongate body.

In one aspect of the embodiment, at least a portion of the optical element is external to the elongate body.

In one aspect of the embodiment, at least a first portion of the optical element is external to the elongate body and at least a second portion of the optical element is within the lumen, the at least a first portion including the FBG.

In one aspect of the embodiment, the medical device is a cryotreatment device, and the medical device further comprises: an expandable element at the distal portion of the elongate body, the expandable element defining a maximum outer diameter; and a distal tip that is distal to the expandable element.

In one aspect of the embodiment, the optical element is on the maximum outer diameter of the expandable element.

In one aspect of the embodiment, the optical element is proximate the distal tip.

In one aspect of the embodiment, the optical element is a first optical element, the medical device further comprising a second optical element, the first optical element being on the maximum outer diameter of the expandable element and the second optical element being one of on and proximate the distal tip.

In one embodiment, a medical system comprises: a medical device, the medical device including: an elongate body including a distal portion and a proximal portion opposite the distal portion; and an optical element located at the distal portion of the elongate body, the optical element including at least one optical fiber having a distal portion and a proximal portion opposite the distal portion and a fiber Bragg grating (FBG) located within the distal portion of the optical fiber; a control unit in communication with the medical device, the control unit including: an optical interrogator in communication with the optical element; and processing circuitry configured to receive data from the optical interrogator.

In one aspect of the embodiment, the medical device is configured to thermally affect tissue, the medical device further including a treatment element at the distal portion of the elongate body, the optical element being coupled to the treatment element.

In one aspect of the embodiment, the treatment element is a balloon defining an equator, the optical element being on the equator of the expandable element.

In one aspect of the embodiment, the medical device is configured to puncture septal tissue, the medical device further including a lumen extending between the proximal portion and the distal portion, at least a first portion of the optical element being external to the elongate body and at least a second portion of the optical element being within the lumen, the at least a first portion including the FBG.

In one embodiment, a method of quantifying a force exerted by a medical device against an area of tissue comprises: placing a distal portion of a medical device in contact with an area of tissue, the medical device including an optical element, the optical element having an optical fiber with fiber Bragg grating; advancing the medical device such that the distal portion of the medical device exerts a force against the area of tissue; obtaining strain data from the optical element with an optical interrogator; transmitting strain data to processing circuitry and correlating the strain data to a pressure value; and repositioning the medical device when the pressure value indicates the distal portion of the medical device is in contact with non-target tissue.

In one aspect of the embodiment, the medical device further includes an elongate body and a puncture element at least partially within the elongate body, and the method further comprises: automatically preventing, by the processing circuitry, advancement of the puncture element from the elongate body and through the tissue when the pressure value indicates the distal portion of the medical device is in contact with non-target tissue.

In one aspect of the embodiment, the medical device is a dilator, wherein the medical device includes a lumen that is sized and configured to receive the puncture element.

In one aspect of the embodiment, at least a portion of the optical element is integrated with an external surface of the elongate body.

In one aspect of the embodiment, the medical device further includes a treatment element configured to cryoablate tissue, and the method further comprises: automatically preventing, by the processing circuitry, circulation of a coolant through the treatment element that is configured to lower a temperature of the treatment element to a temperature that is sufficient to cryoablate tissue.

In one aspect of the embodiment, the medical device includes a treatment element, the treatment element defining an equator, the optical element being on the equator of the treatment element, the step of placing a distal portion of the medical device in contact with an area of tissue including placing at least a portion of the equator of the treatment element in contact with an area of tissue.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
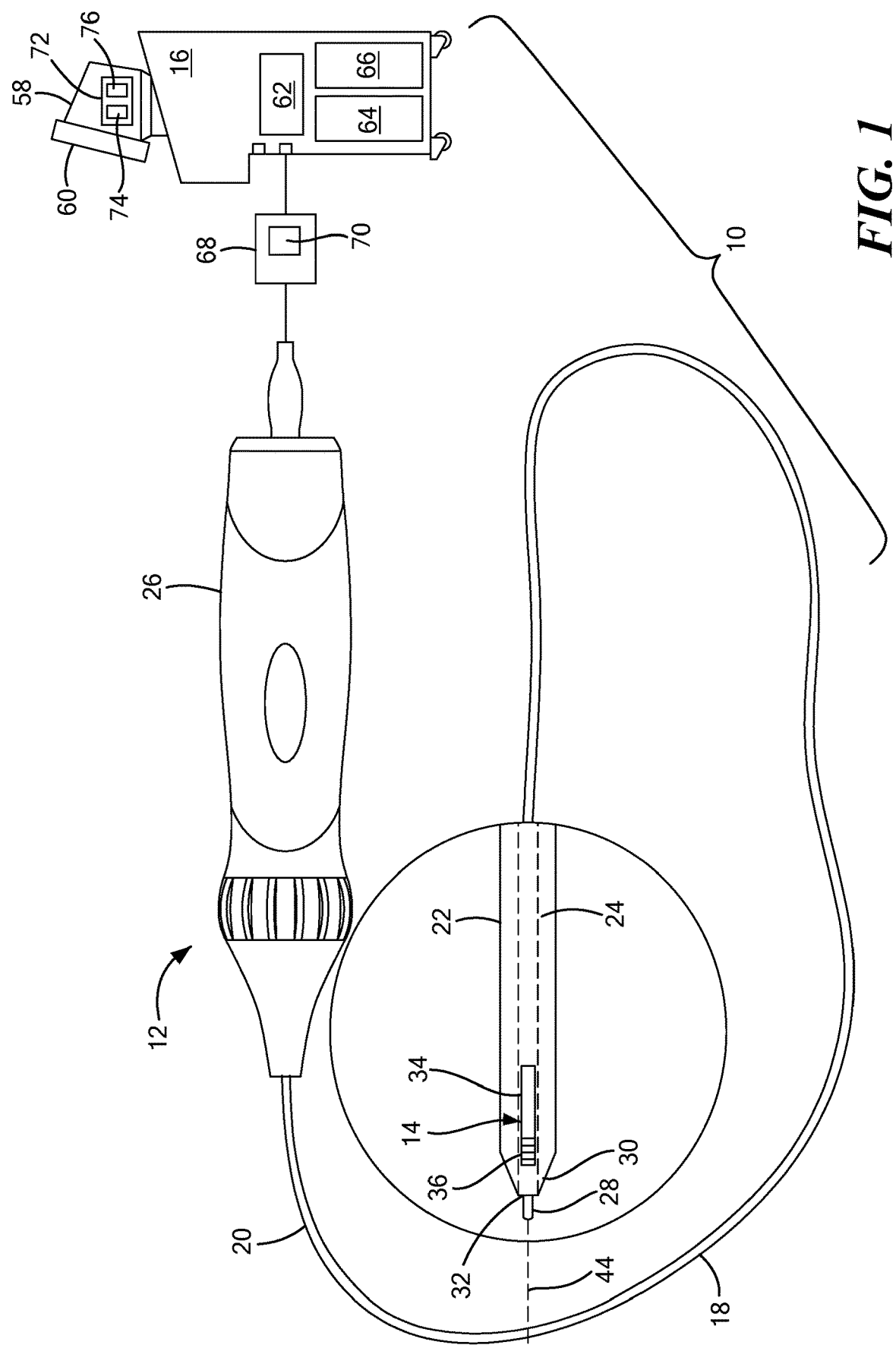
FIG. 1 shows a first exemplary embodiment of a medical system including a medical device with an optical element, in accordance with the present disclosure.

The present invention provides systems and methods of use thereof for quantifying a force exerted against tissue during a medical procedure. For example, the systems and methods of the present disclosure can be used to quantify a linear force exerted on cardiac tissue during a medical procedure such as septal puncture, ablation of an atrial wall and/or pulmonary vein antrum, occlusion of a pulmonary vein with a balloon, or the like, by the inclusion of a fiber optic cable with fiber Bragg grating within a medical device used during the procedure. Referring now to the drawing figures in which like reference designations refer to like elements, FIG. 1 shows an exemplary embodiment of a medical system 10 that includes a device 12 having an optical element 14 for quantifying pressure exerted against an area of tissue, and a control unit 16 for operating, monitoring, and regulating the operation of the device 12 and receiving and processing information from the optical element 14.

Continuing to refer to FIG. 1, the device 12 includes an elongate body 18 having a proximal portion 20, a distal portion 22 opposite the proximal portion 20, and at least one lumen 24 therebetween. In one embodiment, the elongate body 18 is or includes a flexible body suitable for intravascular procedures, such as a catheter body, dilator, delivery sheath, or the like. In some embodiments, the elongate body 18 further includes one or more secondary lumens (not shown) disposed within providing mechanical, electrical, and/or fluid communication between the proximal portion 20 and the distal portion 22 of the elongate body 18. In one embodiment, the proximal portion 20 of the elongate body 18 is be coupled to a handle 26, which may include various ports for electrical and fluid connectors, leads, junctions, or tubes, and may also include various control assemblies, such as switches or valves, as well as safety detection or shutdown components. For example, the handle 26 may include connectors that are matable directly or indirectly by way of one or more umbilicals to the control unit 16. Further, the handle 26 may also include an element such as a lever or knob for manipulating or deflecting at least a portion of the elongate body 18.

Continuing to refer to FIG. 1, in one embodiment the device 12 is a dilator or introducer sheath that is configured to facilitate navigation of a treatment device (such as a cryoablation or radiofrequency ablation catheter) through the patient's vasculature to a target treatment site. In the embodiment shown in FIG. 1, the device 12 is a dilator through which a puncture element 28 can pass, the puncture element being configured to create a puncture in the septum, thereby allowing the device 12 access to the left atrium. For example, once the dilator has passed through the septum and is at least partially positioned the left atrium, a treatment device (not shown) may be passed through the dilator and into the left atrium for a procedure such as pulmonary vein occlusion and/or left atrial ablation. Alternatively, in some procedures, the dilator may be removed and replaced with a delivery sheath (not shown) through which the treatment device may be passed.

Continuing to refer to FIG. 1, in one embodiment the device 12 includes a distal tip 30 including an aperture 32 that is in communication with the lumen 24, and the lumen 24 of the device 12 is sized and configured to at least partially receive the puncture element 28 therein. Additionally or alternatively, the puncture element 28 may be passed through a secondary lumen of the elongate body 18. In one embodiment, the puncture element 28 is longitudinally movable within and through the lumen 24 and may be extended through the distal aperture 32 and distal to the elongate body 18 to create an opening in tissue engaged with the medical device. The puncture element 28 may be any sufficiently pointed component capable of puncturing tissue, such as a needle or trocar. The puncture element 28 may be removably or permanently coupled to the device 12 at either the handle 26 or at any point along the elongate body 16. Further, the puncture element 28 may be disposed within the device 12 in an off-axis manner so as to allow the concurrent passage of a secondary device (or a guide wire) through the lumen 22.

Figure 2:
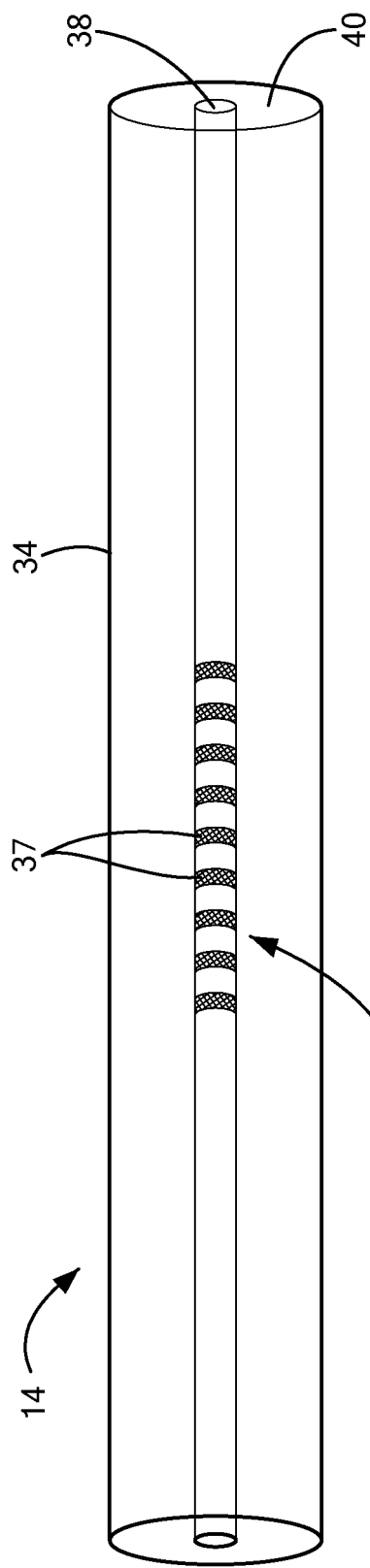
FIG. 2 shows an exemplary optical element, in accordance with the present disclosure.
Figure 3:
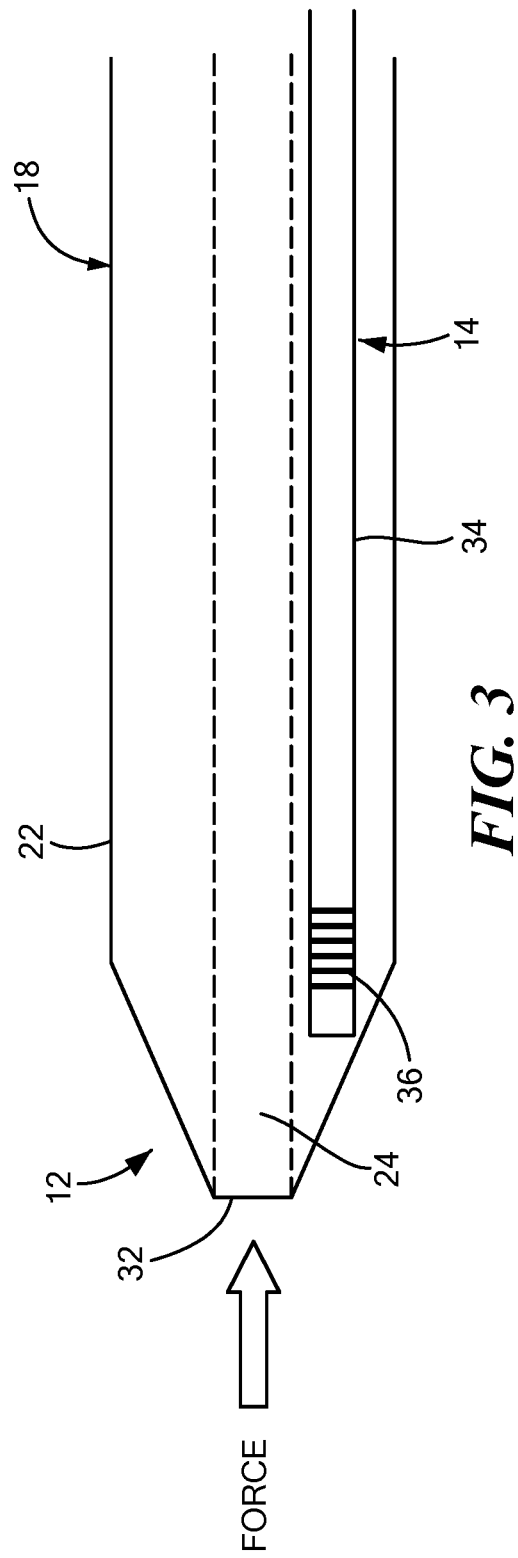
FIG. 3 shows a first embodiment of the medical device of the exemplary medical system shown in FIG. 1, in accordance with the present disclosure.
Figure 4:
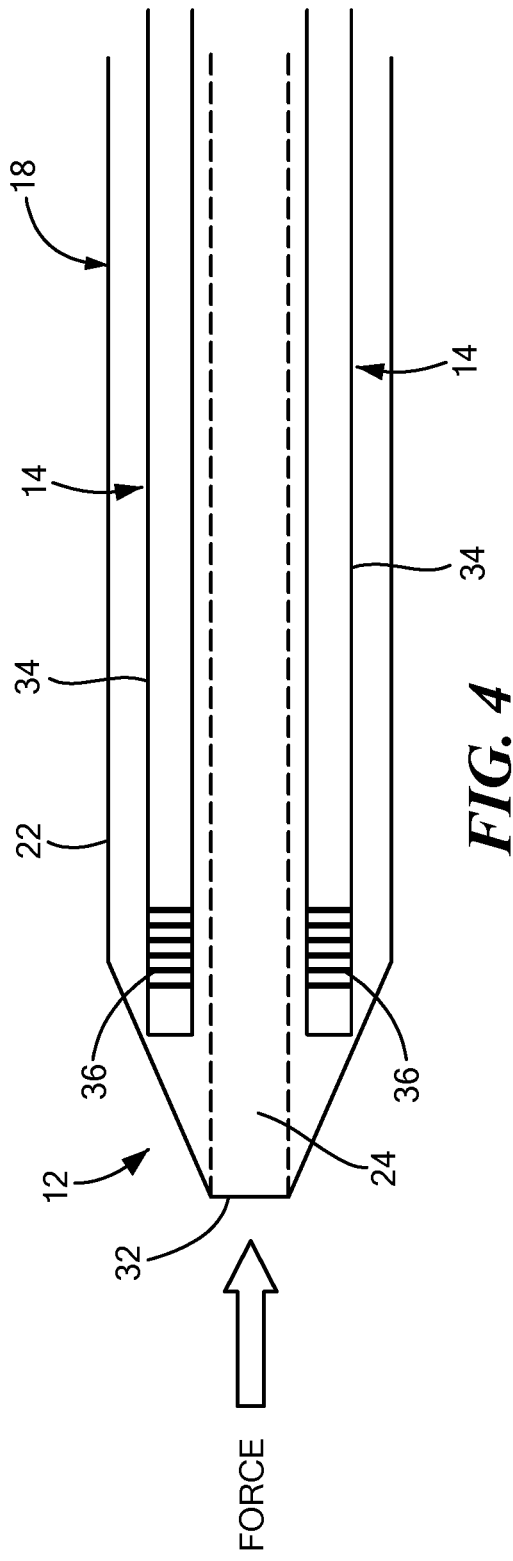
FIG. 4 shows a second embodiment of the medical device of the exemplary medical system shown in FIG. 1, in accordance with the present disclosure.
Figure 5:
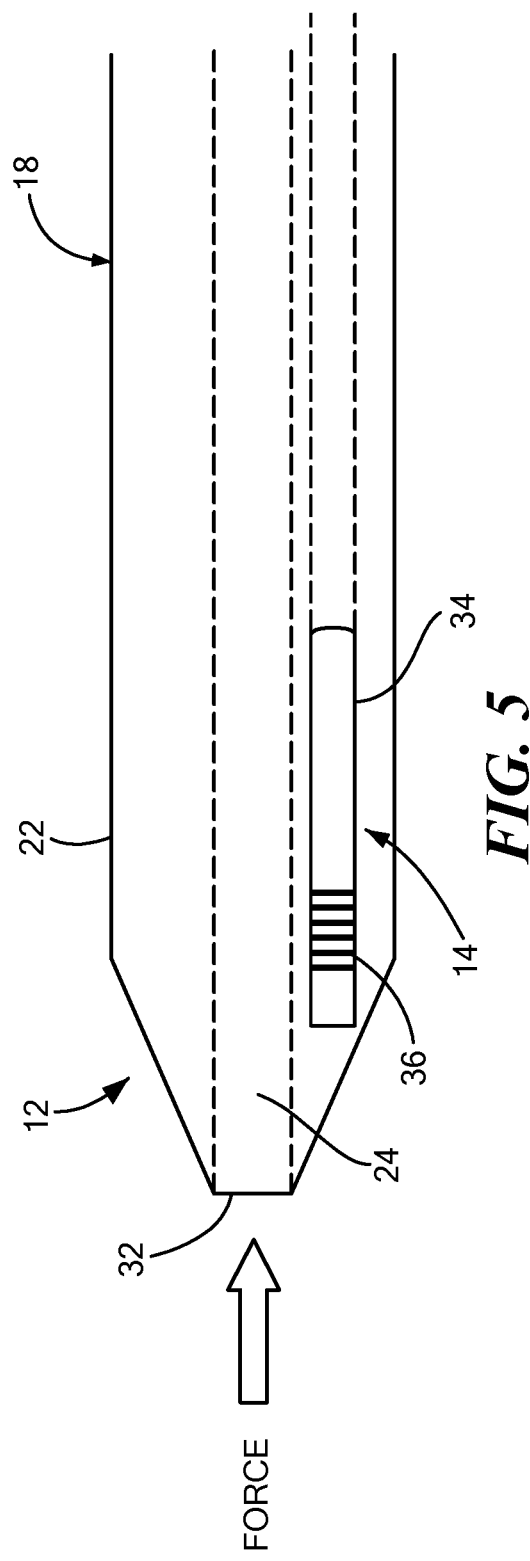
FIG. 5 shows a third embodiment of the medical device of the exemplary medical system shown in FIG. 1, in accordance with the present disclosure.
Figure 6:
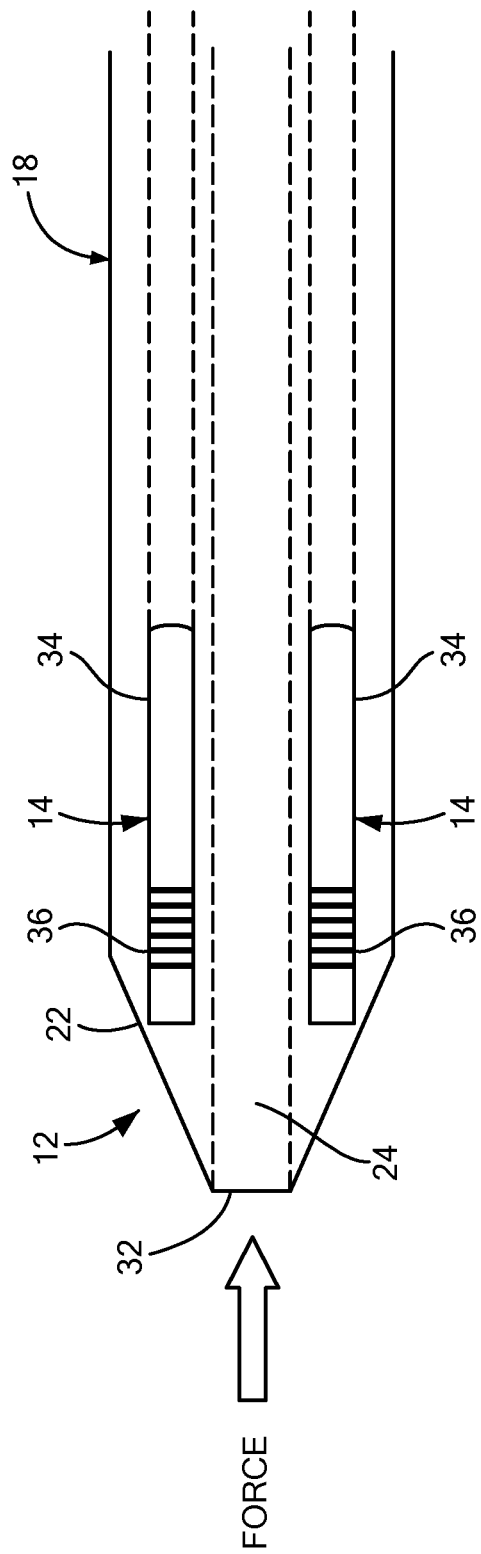
FIG. 6 shows a fourth embodiment of the medical device of the exemplary medical system shown in FIG. 1, in accordance with the present disclosure.

Referring now to FIGS. 2-6, exemplary embodiments of the device 12 of FIG. 1 and the optical element 14 are shown in greater detail. FIG. 2 shows an exemplary optical element 14, FIG. 3 shows a first embodiment of a device 12 including the optical element 14, FIG. 4 shows a second embodiment of a device 12 including the optical element 14, FIG. 5 shows a third embodiment of a device 12 including the optical element 14, and FIG. 6 shows a fourth embodiment of a device 12 including the optical element 14. The devices 12 shown in FIGS. 4 and 6 are substantially the same as the devices 12 shown in FIGS. 3 and 5, respectively, except that the devices 12 of FIGS. 4 and 6 include more than one optical element 14. It will be understood that the device 12 may include any number of optical elements 14 and is not limited to the number, position, and/or configuration of those shown herein. The device 12 is shown in FIGS. 3-6 without the puncture element 28 so as not to unnecessarily complicate the drawings.

Continuing to refer to FIGS. 2-6, In one embodiment, the optical element 14 is operable to sense a pressure exerted on the distal portion 22 of the elongate body 18, such as by an area of tissue (for example, as tissue moves against the distal portion 22 when the heart beats), and/or a pressure exerted by the distal portion 22 of the elongate body 18 against an area of tissue. In one embodiment, the optical element 14 is configured to measure a linear force against the distal tip 32 (for example, as shown in FIGS. 3-6). In one embodiment, the optical element 14 includes at least one optical fiber 34 that includes fiber Bragg grating (FBG) 36 having a plurality of gratings or etched lines 37. In some embodiments (for example, as shown in FIGS. 3 and 5), the at least one optical fiber 34 includes one optical fiber. In other embodiments, the at least one optical fiber 34 includes more than one optical fiber (for example, two optical fibers as shown in FIGS. 4 and 6). In one embodiment, each optical fiber 34 has a core 38 and a cladding 40 surrounding the core 38, and the FBG is etched onto distal portion 42 of the core 38. The FBG is formed by a period change of the refractive index of the core 38 in a direction of propagation of optical radiation, and the FBG acts as a spectral filter that reflects only particular wavelengths of light near Bragg resistance wavelength. Further, the FBG measures certain factors acting against the optical fiber 34, such as mechanical deformation including stretching, pushing, compression, bending, the application of shear stress, or the like. Strain on the optical fiber 34, such as the portion of the optical fiber 34 containing the FBG 36, changes the spacing between gratings of the FBG 36 and, as a result, changes the reflection of light through the optical fiber 34. In one embodiment, the FBG 36 is used to measure a linear pressure or compression force acting along the direction of optical transmission through the optical fiber 34. In one non-limiting example, the FBG 36 is used to measure a pressure or compression force along the longitudinal axis 44 of at least the distal portion 22 of the elongate body 18. Thus, in one embodiment, the optical element 14 functions as a pressure sensor and may be used to facilitate positioning of the device 12 within the patient's body, and may further provide monitoring of the engagement between the device 12 and a designated tissue region during a procedure. The FBG 36 may include any suitable number, thickness, spacing, and/or configuration of gratings. For example, the FBG 36 may be uniform, chirped, or tilted. The optical element 14 shown and described herein is smaller than many other types of pressure sensors and, therefore, may be more easily integrated into or included in a medical device such as a catheter.

In one embodiment of the device 12, as shown in FIGS. 3 and 5, each optical element 14 is integrated with the elongate body 18 and is visible along an entirety of the elongate body 18. In one embodiment, the device 12 is a dilator that is manufactured from a flexible and biocompatible material. In one embodiment, the dilator is composed of a thermoplastic elastomer, such as Pebax® (Arkema France Corporation, France). In exemplary method of manufacturing the dilator, the flexible material (such as thermoplastic elastomer or other suitable materials) is extruded into an elongate component having at least one lumen, the optical fiber 34 is laid along the elongate component such that the FBG 36 will be at the distal portion 22 and, in some embodiments, proximate the distal tip 30, of the elongate body 18 once manufacturing is complete. Further, a heat shrink tubing may then be applied to the elongate body 18 and heated so the flexible material flows and secures the optical element 14 to the elongate body 18 and, in some embodiments, gives the elongate body 18 a continuous or at least substantially continuous outer diameter (that is, so the optical element 14 does not protrude from the elongate body 18). However, it will be understood that the optical element 14 may be removably or permanently attached to the exterior of the elongate body 18, such as by adhesion, mechanical connectors, or the like.

In one embodiment of the device 12, as shown in FIGS. 4 and 6, each optical element is 14 is integrated with the elongate body 18, but only a portion of the optical fiber 34 that includes the FBG 36 is visible. In this embodiment, the remainder of the optical fiber 34 of each optical element 14 is located within the lumen 22 or a secondary lumen. In exemplary method of manufacturing the dilator, the flexible material (such as thermoplastic elastomer or other suitable materials) is extruded into an elongate component having at least one lumen, and a small hole 46 is created in the elongate component that places the lumen 22 or secondary lumen in communication with an environment external to the elongate component. In one embodiment, the hole 46 is located in a distal portion of the elongate component. The optical fiber 34 is fed through the lumen 22 or secondary lumen, then passed through the hole 46 so a portion of the optical fiber 34 including the FBG 36 is laid along an external surface of the elongate component such that the FBG 36 will be at the distal portion 22 and, in some embodiments, proximate the distal tip 30, of the elongate body 18 once manufacturing is complete. Further, a heat shrink tubing may then be applied to the elongate body 18 and heated so the flexible material flows and secures the exposed portion of the optical element 14 to the elongate body 18 and, in some embodiments, gives the elongate body 18 a continuous or at least substantially continuous outer diameter (that is, so the optical element 14 does not protrude from the elongate body 18). However, it will be understood that the portion of the optical element 14 including the FBG 36 may be removably or permanently attached to the exterior of the elongate body 18, such as by adhesion, mechanical connectors, or the like. It will further be understood that in some embodiments no part of the optical element 14 is exposed. For example, an entirety of the optical element 14 may be within a lumen of the elongate body 18 and/or embedded within the material from which the elongate body 18 is composed.

Figure 7:
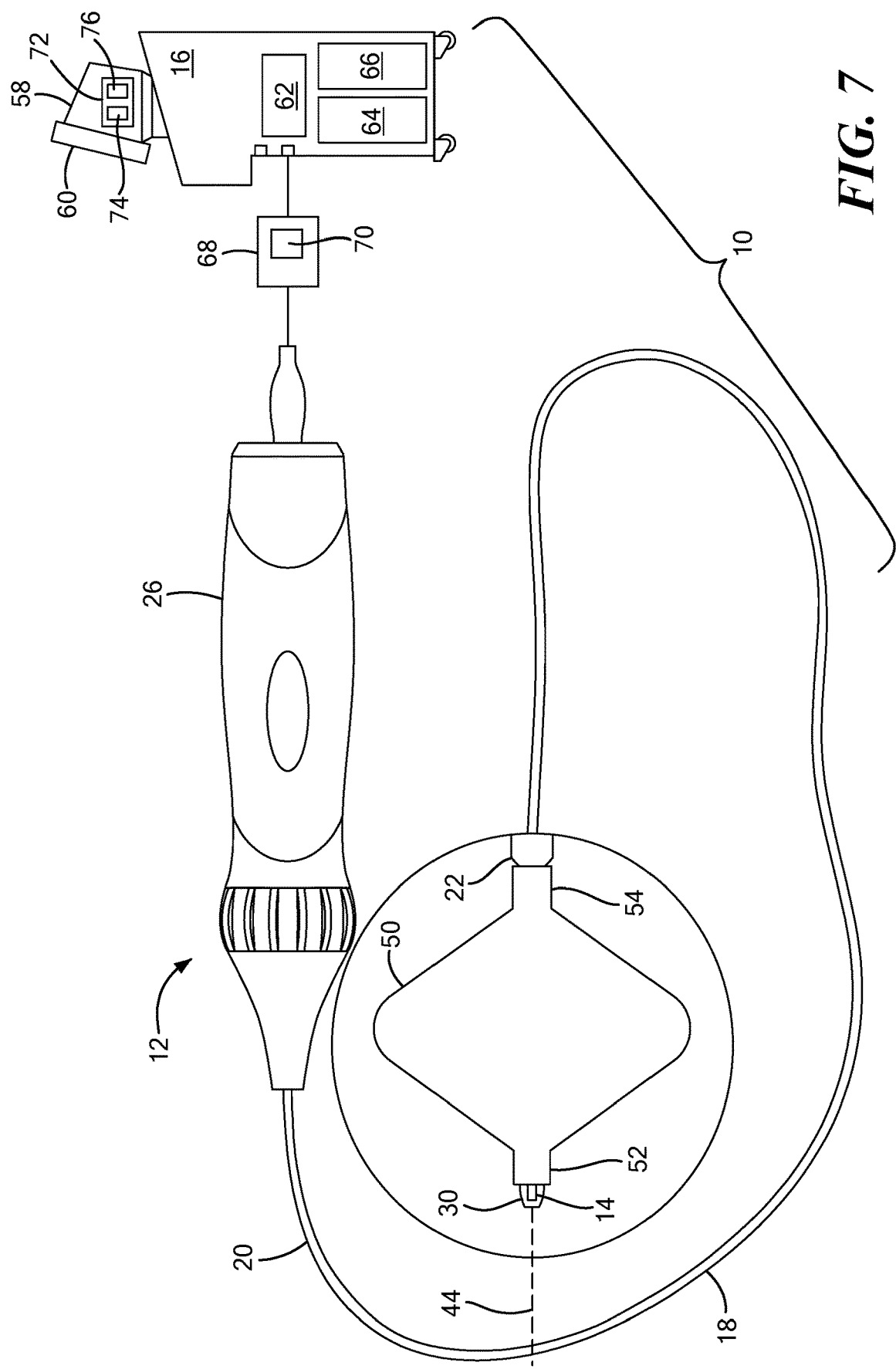
FIG. 7 shows a second exemplary embodiment of a medical system including a medical device with an optical element, in accordance with the present disclosure.
Figure 8:
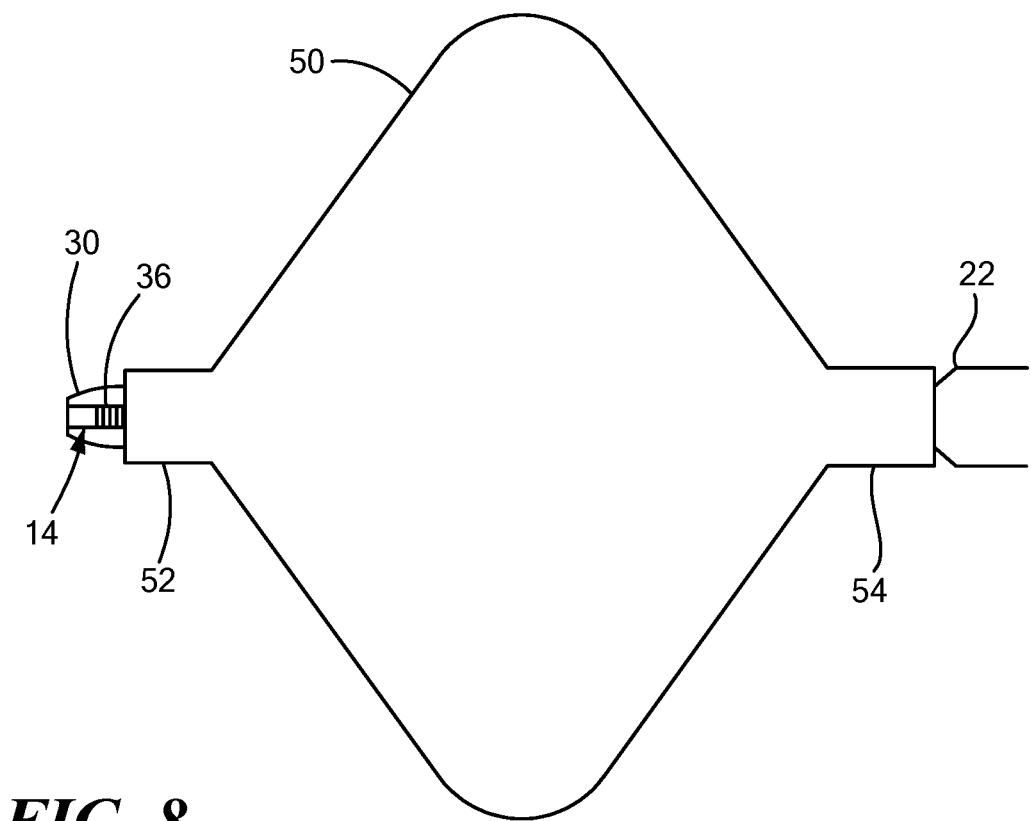
FIG. 8 shows a first embodiment of the medical device of the exemplary medical system shown in FIG. 7, in accordance with the present disclosure.
Figure 9:
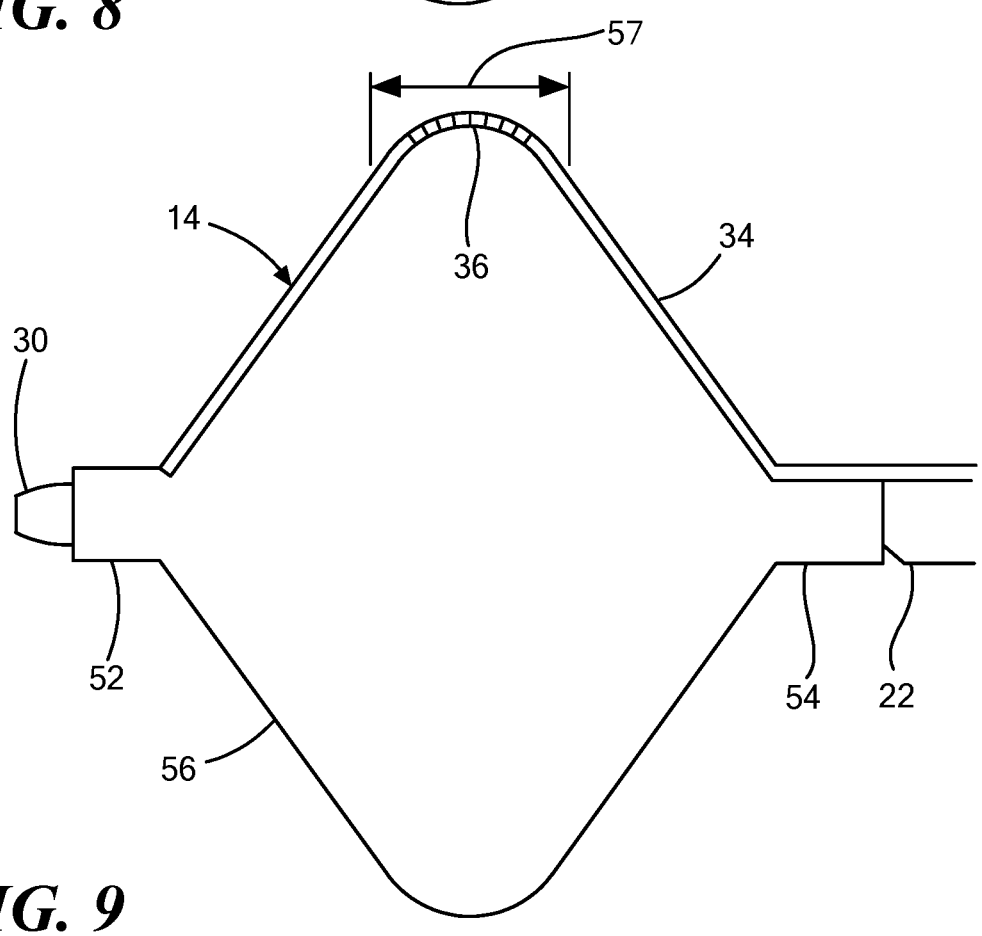
FIG. 9 shows a second embodiment of the medical device of the exemplary medical system shown in FIG. 7, in accordance with the present disclosure.
Figure 10:
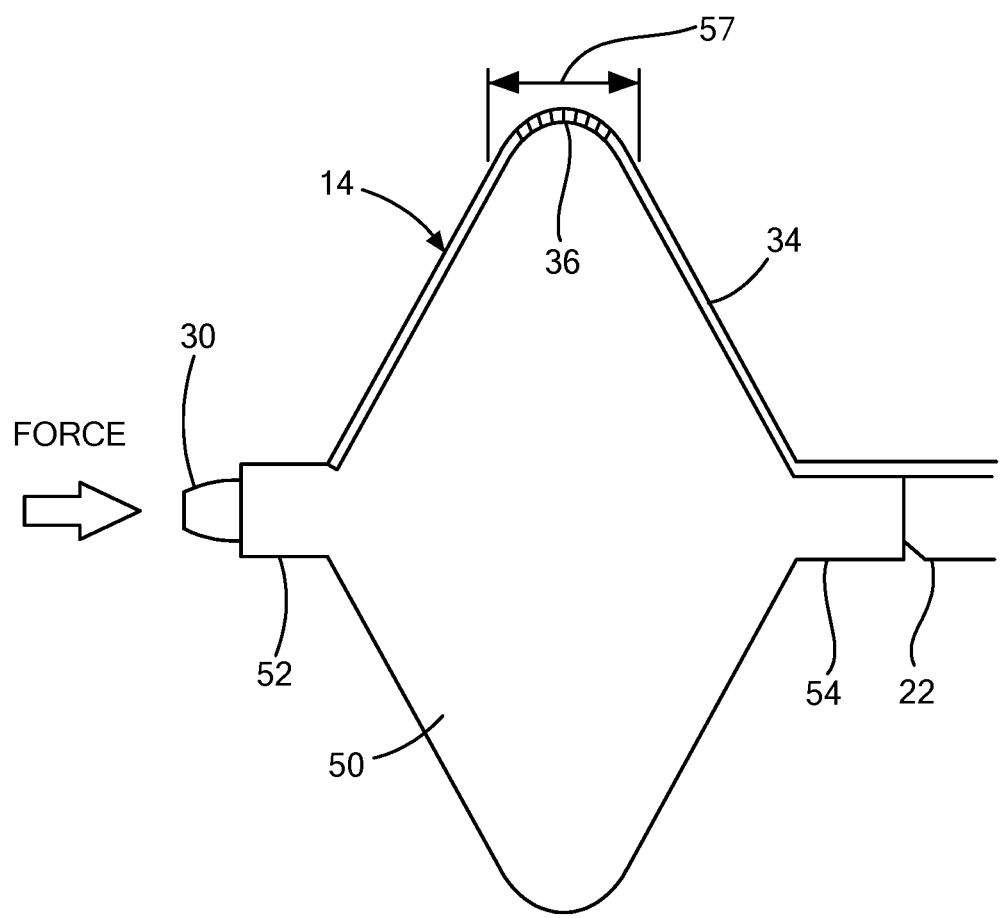
FIG. 10 shows the medical device of FIG. 9, the medical device being compressed.
Figure 11:
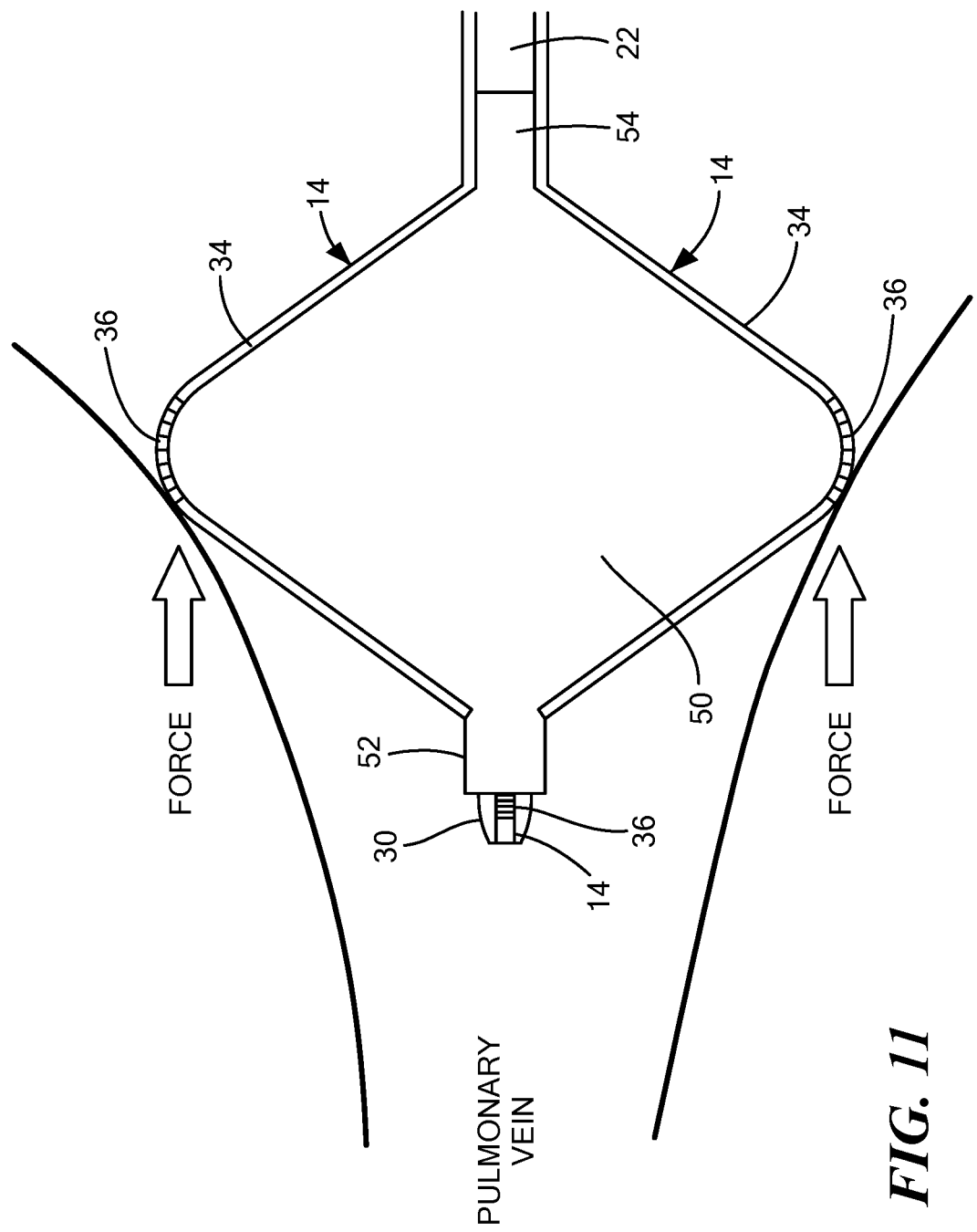
FIG. 11 shows a third embodiment of the medical device of the exemplary medical system shown in FIG. 7, in accordance with the present disclosure, the medical device being positioned in contact with a pulmonary vein ostium.
Figure 12:
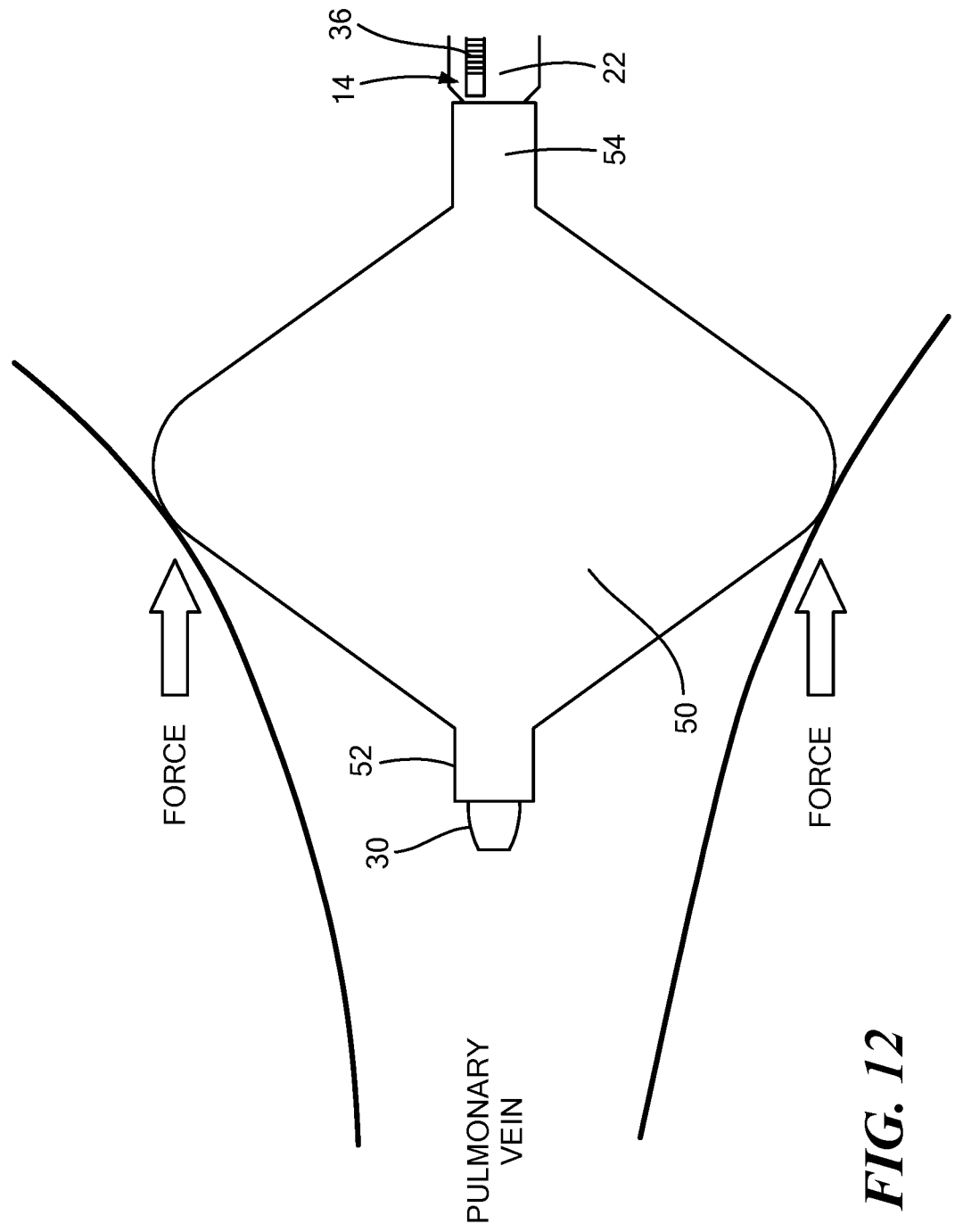
FIG. 12 shows a fourth embodiment of the medical device of the exemplary medical system shown in FIG. 7, in accordance with the present disclosure, the medical device being positioned in contact with a pulmonary vein ostium.
Figure 13:
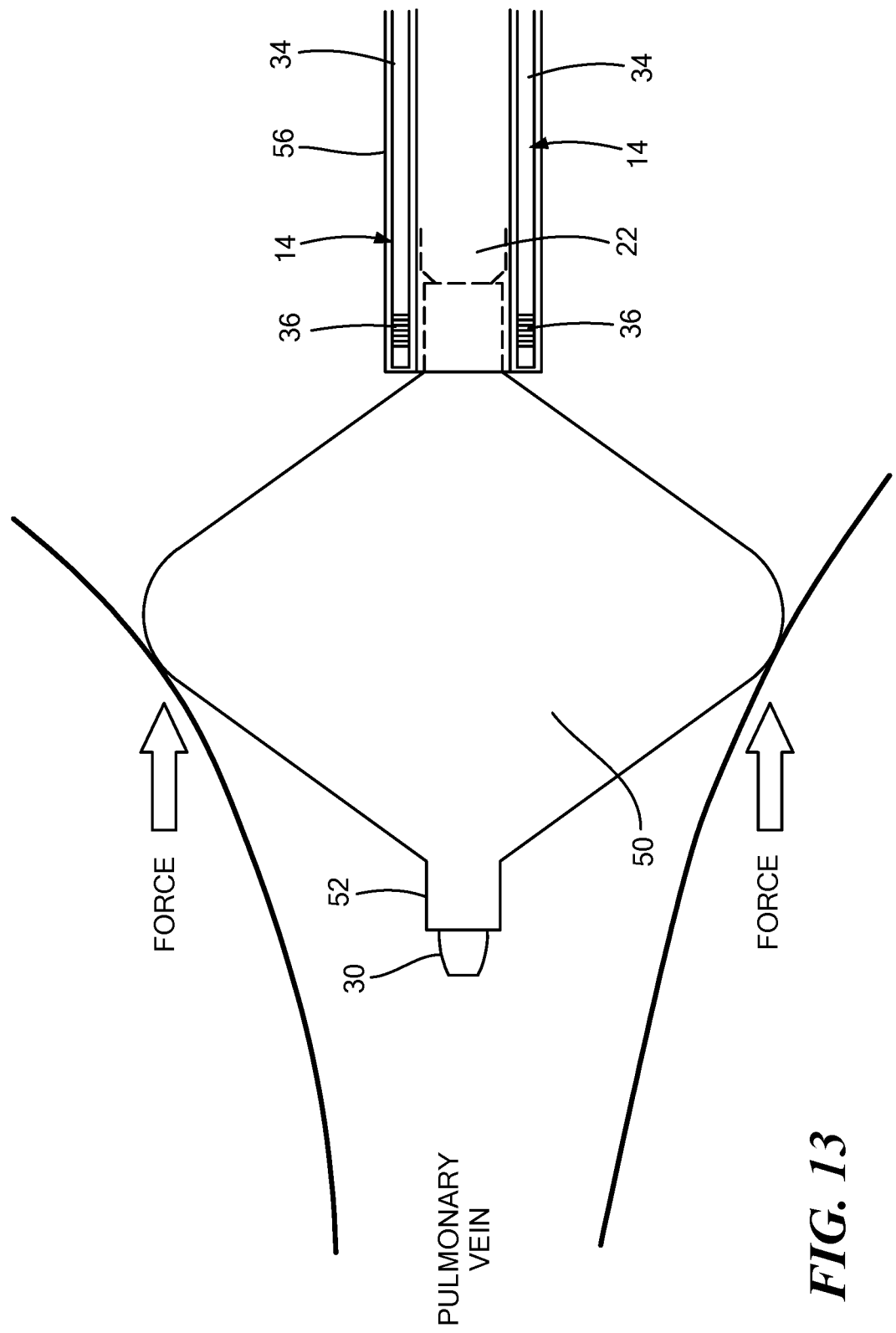
FIG. 13 shows a fifth embodiment of the medical device of the exemplary medical system shown in FIG. 7, in accordance with the present disclosure, the medical device being positioned in contact with a pulmonary vein ostium.

Referring now to FIGS. 7-13, a second exemplary embodiment of a medical system 10 that includes a device having an optical element 14 and exemplary embodiments of the device 12 are shown. FIG. 7 shows the second embodiment of the medical system 10, FIG. 8 shows a first exemplary embodiment of the device 12 including the optical element 14 for use with the medical system 10 of FIG. 7, FIG. 9 shows a second exemplary embodiment of the device 12 including the optical element 14 for use with the medical system 10 of FIG. 7, FIG. 10 shows the medical device of FIG. 9 compressed by an applied force, FIG. 11 shows a third embodiment of the device 12 including the optical element 14 for use with the medical system 10 of FIG. 7 and with the device 12 positioned against an area of tissue, FIG. 12 shows a fourth embodiment of the device 12 including the optical element 14 for use with the medical system 10 of FIG. 7 and with the device 12 positioned in contact with an area of tissue, and FIG. 13 shows a fifth embodiment of the device 12 including the optical element 14 for use with the medical system 10 of FIG. 7 and with the device 12 positioned in contact with an area of tissue. In one embodiment the medical system 10 is configured to deliver cryotherapy. Thus, in one embodiment, the device 12 is a cryotreatment catheter that is configured to be navigated through the patient's vasculature (for example, with or without use of a delivery sheath or other device) to a target treatment site. In the embodiment shown in FIG. 7, the device 12 is a cryotreatment catheter having at least one treatment element 48 for thermally affecting an area of target tissue. In one embodiment, the at least one treatment element 48 includes at least one expandable element 50, such as a balloon, coupled to the distal portion 22 of the elongate body 18. In one embodiment, the expandable element 50 includes a distal neck 52 and a proximal neck 54, one or both of which being coupled to the elongate body 18.

Referring to FIGS. 8-13, the optical element(s) 14 may be in one or more locations on the device 12. For example, in some embodiments of the device 12, the optical element(s) 14 are integrated with and/or disposed on at least a portion of the distal tip 30 (for example, as shown in FIG. 8), the expandable element 50 (for example, as shown in FIGS. 9-11), the distal portion 22 of the elongate body 18 of a device 12 having an expandable element 50 (for example, as shown in FIG. 12), and/or a distal portion 22 of an elongate body 18 such as a delivery sheath or dilator (for example, as shown in FIG. 13). However it will be understood that, in some embodiments, the device 12 includes more than one optical element 14 at a combination of locations. In one non-limiting example, the device 12 may include a plurality of optical elements 14 on the expandable element 50 and an optical element 14 on the distal tip 30 (as shown in FIG. 11). Alternatively, the device 12 of FIG. 11 may include only the optical elements 14 on the expandable element 50. As a further non-limiting, the device 12 may include a first optical element 14 positioned as shown in FIG. 8 and a second optical element 14 positioned as shown in FIG. 12. As a further non-limiting example, the device 12 may include one or more optical elements 14 (for example, as shown in FIG. 11) and may be used with a delivery sheath 56 having one or more optical elements 14 (for example, as shown in FIG. 13). It will also be understood that other combinations are contemplated.

Referring to FIG. 8, in one embodiment the optical element(s) 14 are affixed to or integrated with the device 12 such that the FBG 36 is at or proximate the distal tip 30. FIG. 8 shows a device 12 having one optical element 14, but it will be understood that more than one optical element 14 may be used. A force exerted by the device 12 against an area of tissue or from the area of tissue against the device 12, such as an axial force, strains or affects the spacing between gratings 37 of the FBG 36 and this strain value may be correlated to an applied force value by the system 10, such as is described below.

Referring to FIGS. 9-11, in some embodiments, the optical element(s) 14 are affixed to or integrated with the expandable element 50. For example, in one embodiment (as shown in FIG. 9), one optical fiber 34 is adhered to an outer surface of the expandable element 50, integrated with the material of the expandable element 50, or otherwise disposed on or at least partially within the material the expandable element 50 such that the FBG 36 is positioned to measure a force exerted by the expandable element 50 against an area of tissue or by the area of tissue against the expandable element 50. As shown in FIG. 10, a force (such as an axial force) may compress the expandable element 50, which in turn compresses or otherwise affects the FBG 36 and spacing between gratings 37. In one embodiment, the expandable element 50 defines an equator 57 (that is, an area of largest outer diameter) when the expandable element 50 is inflated or expanded. In some exemplary methods of use, at least a portion of the equator 57 is configured to contact an area of tissue, such as a pulmonary vein ostium and/or antrum (for example, as shown in FIG. 11). In one embodiment, the FBG 36 is located on the equator 57 of the expandable element 50. Further, in some embodiments, the FBG 36 is located on a distal face of the expandable element 50 when the expandable element 50 is inflated or expanded.

Placement of the expandable element 50 at least partially in contact with the pulmonary vein ostium and/or antrum causes a force to be exerted against at least a portion of the expandable element 50, and the resulting strain value may be correlated by the system 10 to an applied force value. Further, the applied force value and/or location of the applied force against the expandable element 50 may be used to determine whether the pulmonary vein is sufficiently occluded.

Referring to FIG. 12, in one embodiment, the optical element(s) 14 are located such that the FBG 36 of each optical element 14 is located proximal to the expandable element 50 when the device 12 is in use, such as on a distal portion 22 of the elongate body 18 to which the expandable element 50 is attached. Although one optical element 14 is shown in FIG. 12, it will be understood that more than one optical element 14 may be used. When a force (such as an axial force is exerted by or against the expandable element 50, that force is transferred to the elongate body 18 of the device 12 and, therefore, the optical element(s) 14. As noted above, the optical element(s) 14 record a strain value and the system 10 correlates the strain value to an applied force value.

Referring to FIG. 13, the optical element(s) 14 are located such that the FBG 36 of each optical element 14 is located and/or on a distal portion 22 of an elongate body 18 of a delivery sheath, dilator, or other device 56 through which the device 12 is passed. Although one optical element 14 is shown in FIG. 13, it will be understood that more than one optical element 14 may be used. When a force (such as an axial force is exerted by or against the expandable element 50, that force is transferred to the delivery sheath 56 and, therefore, the optical element(s) 14. As noted above, the optical element(s) 14 record a strain value and the system 10 correlates the strain value to an applied force value.

Referring now to FIGS. 1 and 7, in one embodiment the control unit 16 is in fluid and/or electrical communication with the medical device 12, including the optical element 14. As used herein, the term "control unit 16" may be used to include any components of the medical system 10 other than the device 12, regardless of whether those components are physically located within the control unit 16. For example, the medical system 10 may include one or more relay boxes, computers, additional electrodes, generators, or other components that may be in communication with, but not located within a housing of, the control unit 16. In one embodiment, the control unit 16 includes one or more computers 58 with displays 60, and may further include various other displays, screens, user input controls, keyboards, buttons, valves, conduits, sensors, connectors, power sources, energy generators, processors, and computers for adjusting and monitoring system parameters. For example, in some embodiments, and depending on the intended use of the medical system 10, the control unit 16 includes an energy generator 62, as shown in FIGS. 1 and 7, and one or more fluid reservoirs (such as a coolant source reservoir 64 and a coolant recovery reservoir 66, as shown in FIG. 7). Further, the medical system 10 may also include and/or be in communication with one or more systems for visualizing the device 12 within the patient's body, such as a mapping system, X-ray system, fluoroscopic imaging system, magnetic resonance imaging (MRI) system, computerized tomography (CT) system, and/or the like. As used herein, the term "computer" may refer to any programmable data-processing unit, including a smart phone, dedicated internal circuitry, user control device, or the like.

Continuing to refer to FIGS. 1 and 7, the medical system 10 includes a data acquisition system referred to herein as an optical interrogator 68 that is in communication with the optical element 14. Further, in embodiments in which the device 12 in includes more than one optical element 14, the optical interrogator 68 is in communication with all of the optical elements 14, and may acquire data from the optical elements 14 simultaneously using the same or different sampling rates. The optical interrogator 68 is an optoelectronic device that interrogates the FBG 36 and receives and interprets data from the FBG 36 based on light reflected by gratings of the FBG 36. In one embodiment, the optical interrogator 68 includes a light source 70, and applies light in one or more wavelengths from the light source 70 through the optical fiber 34 to the FBG 36. The FBG 36 acts as a filter and disallows passage of certain wavelengths of light according to the spacing between the gratings 37 of the FBG 36. When the FBG 36 becomes compressed (such as when force is exerted against a portion of the device 12 and, as a result, the FBG 36), the spacing between the gratings 37 is reduced and the wavelength that is allowed to pass therethrough is also reduced. The wavelength measurement of light returning through the optical fiber 34 to the optical interrogator 68 provides information about how compressed (shorter wavelength) or extended (longer wavelength) the optical fiber 34 has become and, therefore, how much strain is applied to the optical fiber 34. In some embodiments, the medical system 10 further includes one or more optical filters (not shown) between the device 12 and the optical interrogator 68.

Continuing to refer to FIGS. 1 and 7, in one embodiment the computer 58 includes processing circuitry 72 having a processor 74 and a memory 76. The memory 76 is in electrical communication with the processor 74 and has instructions that, when executed by the processor 74, configure the processor 74 to execute at least one algorithm for receiving, processing, and/or analyzing strain measurements, pressure measurements, or other measurements of physical force measured by the optical element 14. In one embodiment, the processing circuitry 72 is in communication with and receives data from the optical interrogator 68. In some embodiments, the memory 76 includes a lookup table and the processing circuitry 72 is configured to compare strain or pressure measurements received from the optical element 14 to data in the lookup table and/or other source of known data (referred to herein as reference data or reference values) and to determine whether the device 12 is being applied against an area of tissue with insufficient, adequate, or excess force. Likewise, in some embodiments the processing circuitry 72 is configured to compare measured data to reference data to determine whether the device 12 is being applied against tissue in a target location or a non-target location. For example, when performing septal puncture, it may be desired that the tip of the puncture element or dilator be applied against the fossa ovalis, which is thinner and more compliant than surrounding septal tissue. However, the tip of the puncture element or dilator may become trapped or bound by pectinated muscles adjacent the fossa ovalis, which muscles are thicker and harder to puncture. Thus, if more force is exerted against the septum when attempting to create a septal puncture, data from the optical element 14 may indicate that the puncture element and/or dilator are at a non-target location (that is, not exerting a force against the fossa ovalis). In one embodiment, the processing circuitry 72 displays on a display 60 raw data received from the optical element 14 and/or data processed by the processing circuitry 72, and/or generates an alert to the user (for example, an audio, visual, and/or text alert, and/or through the use of haptic feedback in the handle 24).

Continuing to refer to FIGS. 1 and 7, in some embodiments, the processing circuitry 70 is also in communication with one or more other sensors in the medical system 10, such as temperature sensors, flow sensors, impedance sensors, or the like. In fact, in one embodiment, the optical element 14 may also be used to measure temperature from tissue and/or blood surrounding the optical element 14. For example, in one embodiment the device 12 may include an expandable element 50 and an optical element 14 on or integrated with the expandable element 50, which would allow measurement of tissue in contact with the expandable element 50. In some embodiments, the processing circuitry 70 is also in communication with one or more energy generators 62, valves, and other components of the medical system 10.

It will be understood that the medical system 10 may be used with at least one energy modality in addition to or instead of cryotherapy, such as radiofrequency energy, pulsed field ablation energy, laser energy, electroporation energy, microwave energy, or others. That is, the medical systems shown in FIGS. 1 and 7 are exemplary only and are provided to give context to the disclosure, and it will be understood that the optical element 14 disclosed herein may be used with a medical device configured to engage tissue, regardless of the target tissue location, energy modality used, configuration of the device and/or treatment element, or the like. Likewise, the devices 12 shown herein may be used with the system of FIG. 1, the system of FIG. 7, and/or other medical systems. As non-limiting examples, the optical element 14 disclosed herein may be included on a device configured for radiofrequency ablation and having a treatment element that includes an expandable electrode array, a device configured for spot ablation of atrial tissue and having a single distal tip electrode, a device configured for tissue mapping and having a treatment element that includes a non-expandable mapping electrode array, or any other medical device during use of which measuring force exerted by or against tissue would be advantageous.

Figure 14:
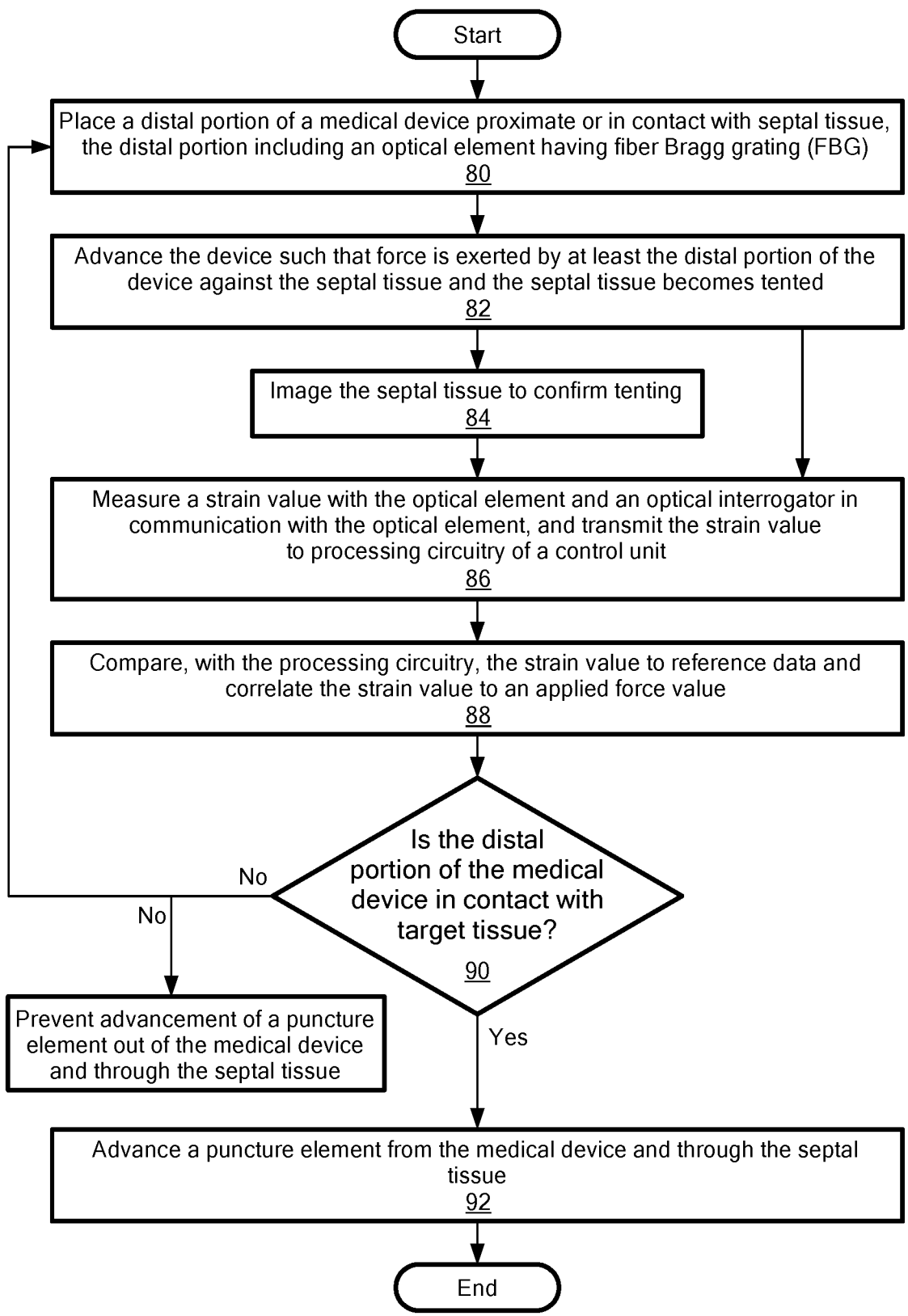
FIG. 14 shows a flowchart of a first exemplary method of use of a medical system including a device with an optical element, in accordance with the present disclosure.
Figure 15:
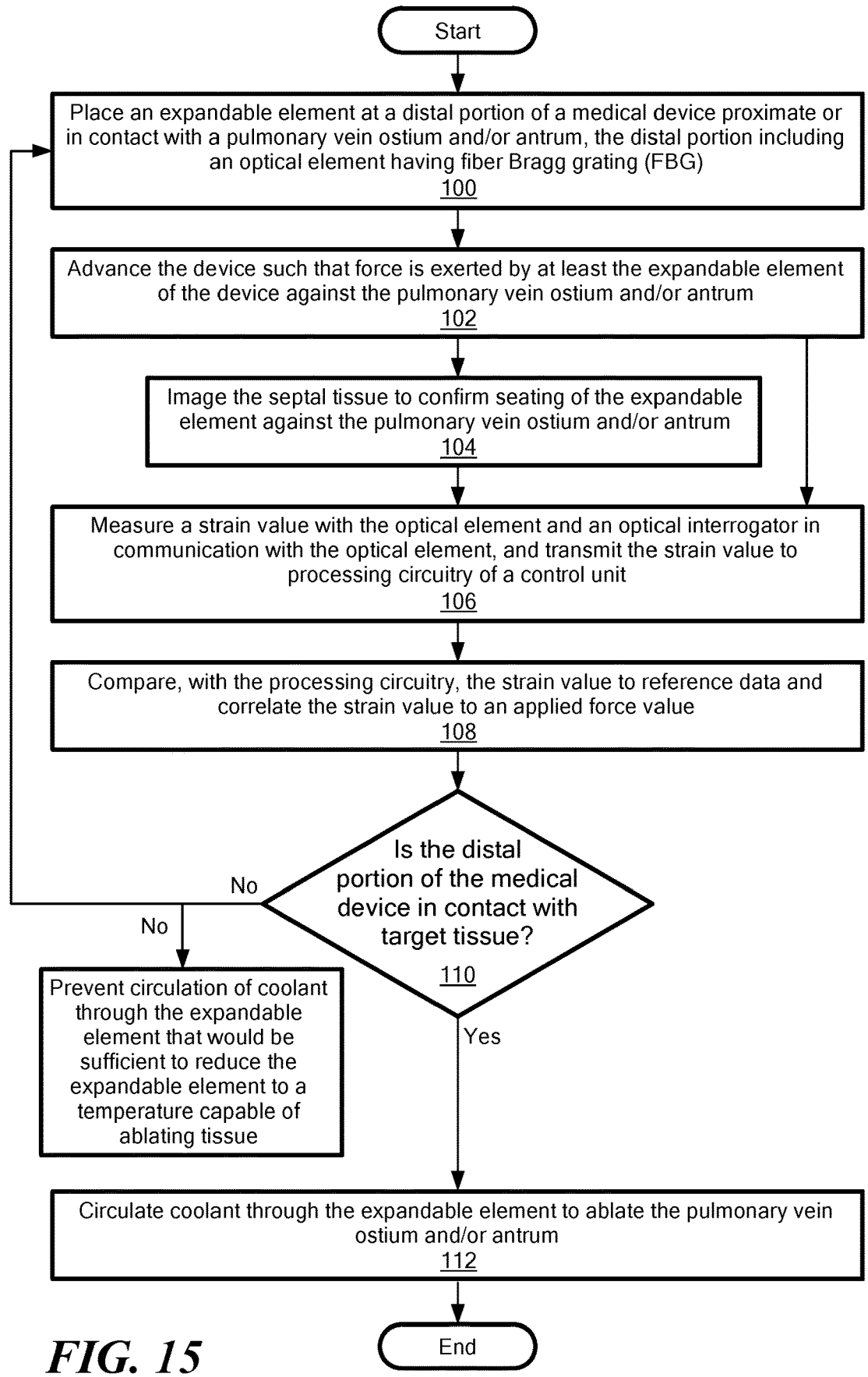
FIG. 15 shows a flowchart of a second exemplary method of use of a medical system including a device with an optical element, in accordance with the present disclosure.

Referring now to FIGS. 14 and 15, exemplary methods of use of the medical system 10 are shown. In general, the optical element 14 of the medical system 10 may be used to provide feedback to the user during a procedure, such as a quantification of a force or strain value between the device 12 and the tissue with which the device 12 is in contact. For example, this feedback may be used for user training, as it may help the user learn or understand when the device 12 is being pressed against an area of tissue with excessive force, which, in turn, may indicate not only a possibility of patient injury, but also whether the device 12 is properly positioned relative to a target tissue location. As another example, during an ablation procedure, it may be undesirable to apply electrodes of the treatment element 48 against tissue with too much force, as this may affect delivery (for example, bipolar delivery) of energy to the tissue. As a further example, a balloon or other expandable element 50 is pressed against a pulmonary vein ostium during a pulmonary vein occlusion procedure. The expandable element 50 must be pressed against the tissue with sufficient force to occlude the pulmonary vein and prevent blood from flowing past the expandable element 50 and into the left atrium, but too much force may cause damage to the tissue and patient injury. Once the expandable element 50 is properly placed and the pulmonary vein is occluded, the circulation of coolant through the expandable element 50 sufficient to cause cryoablation may commence. Thus, the feedback provided by the optical element 14 may be used to automatically or semi-automatically adjust operating parameters of the medical system 10, such as voltage of delivered energy, the circulation of coolant through a balloon of the treatment element 48, or the like.

Referring to FIG. 14, an exemplary method of performing transseptal puncture with a device 12 including an optical element 14 is shown. First, a distal portion of a medical device 12 such as a dilator is placed proximate or in contact with an area of tissue (Step 80), such as the septum. In one embodiment, the distal portion 22 of the device includes the optical element 14. The user then advances the device 12 such that a force is exerted by at least the distal portion 22 of the device 12 against the septum, or by the septum against the device 12 (Step 82). The distal portion 22 of the device 12 is exerted with sufficient force to tent or deform the septum into the left atrium. As noted above, the fossa ovalis is typically a target for transseptal puncture, as it is thinner, more compliant, and easier to puncture than the thicker surrounding tissue. Optionally, the tissue may be imaged to confirm tenting of the septum, such as by using X-ray, computed tomography (CT), magnetic resonance (MRI), angiography, or other non-invasive imaging methods (Step 84).

Continuing to refer to FIG. 14, the force exerted on the device 12 and, therefore, by the device 12 against the tissue, is measured by the FBG 36 and communicated to the optical interrogator 68 (Step 86). That is, the optical interrogator 68 applies light to the optical fiber 34, receives reflected light from the FBG 36 through the optical fiber 34, and correlates the reflected light to a strain value. The optical interrogator 68 then transmits the raw data and/or correlated data (strain value) to the processing circuitry 72 of control unit 16. The processing circuitry 72 then compares the strain value(s) received from the optical interrogator to reference data, correlates strain data to an applied force value, and generates an alert signal that is communicated to the user (Step 88). In one embodiment, the alert signal is displayed visually on the display 60 and provides the user with an indication of the amount of pressure being applied by the device 12 against the tissue. For example, the alert signal may be displayed as numbers showing an applied force, a graphical representation of the tented tissue with superimposed indicia indicating applied force value(s), an icon indicating into which range of applied forces the actual applied force falls, or the like. Additionally or alternatively, the processing circuitry 72 may compare strain data to reference data and to visualization of the tissue performed by one or more imaging systems to determine whether the applied force and resulting amount of tenting or deformation of the tissue indicates that the device 12 is being pressed against the fossa ovalis (target tissue) or surrounding tissue (non-target tissue), and generates an alert signal to communicate this determination to the user. For example, a force exerted against the fossa ovalis may produce a greater amount of deformation in the septum than the same force exerted against the thicker tissue surrounding the fossa ovalis.

Continuing to refer to FIG. 14, if the processing circuitry 72 determines that the device 12 is being pressed against non-target tissue, the user receives this determination as an alert signal and repositions the device 12 (Step 90) before advancing the puncture element 28 out of the elongate body 18 and through the tissue. In one embodiment, Steps 1-5 are then repeated until the processing circuitry 72 determines that the device 12 is being pressed against target tissue. In one embodiment, the processing circuitry 72 is configured to issue a warning to the user to prevent advancement of the puncture element 28. In another embodiment, the processing circuitry 72 is configured to automatically prevent advancement of the puncture element 28 out of the elongate body 18 and through the tissue and avoid unintentional tissue damage and patient injury. Once the processing circuitry 72 determines that the device 12 is being pressed against target tissue, this information is communicated to the user and the user advances the puncture element 28 out of the elongate body 18 and through the septum (for example, the fossa ovalis) (Step 92). The device 12 may then be advanced through the puncture to widen the puncture, and then one or more treatment devices may be advanced through the puncture to access the left atrium.

Referring to FIG. 15, an exemplary method of performing pulmonary vein occlusion with a device 12 including an optical element 14 is shown. First, at least a portion of a treatment element 48 at the distal portion 22 of a medical device 12 is placed in contact with an area of tissue (Step 100), such as an area of tissue surrounding a pulmonary vein ostium. In one embodiment, the device is a cryotreatment catheter and the treatment element 48 includes at least one expandable element 50, such as a balloon. In one embodiment, the distal portion 22 of the device 12 and/or an equator 57 of the expandable element 50 includes the optical element 14. The user then advances the device 12 such that a force is exerted by the treatment element 50 (for example, the equator 57) against a pulmonary vein ostium and/or antrum, or by the pulmonary vein ostium and/or antrum against the treatment element 50 (Step 102). The expandable element 50 of the device 12 is exerted with sufficient force to occlude the pulmonary vein and prevent blood within the pulmonary vein from flowing around the expandable element 50 and into the left atrium. Complete occlusion helps assure that the expandable element 50 will cause adequate lesion formation around the pulmonary vein ostium. If occlusion is incomplete, warm blood may escape into the left atrium and warm the expandable element 50 as it passes. Optionally, the tissue may be imaged to confirm occlusion of the pulmonary vein, such as by using fluoroscopy, X-ray, computed tomography (CT), magnetic resonance (MRI), angiography, or other non-invasive imaging methods (Step 104).

Continuing to refer to FIG. 15, the pressure exerted on the device 12 and, therefore, by the expandable element 50 against the tissue, is measured by the FBG 36 and communicated to the optical interrogator 68 (Step 106). That is, the optical interrogator 68 applies light to the optical fiber 34, receives reflected light from the FBG 36 through the optical fiber 34, and correlates the reflected light to a strain value. The optical interrogator 68 then transmits the raw data and/or correlated data (strain value) to the processing circuitry 72 of control unit 16. The processing circuitry 72 then compares the data received from the optical interrogator to reference data, correlates strain data to an applied force value, and generates an alert signal that is communicated to the user (Step 108). In one embodiment, the alert signal is displayed visually on the display 60 and provides the user with an indication of the amount of pressure being applied by the device 12 against the tissue. For example, the alert signal may be displayed as numbers showing an applied force, a graphical representation of the expandable element 50 against the tissue with superimposed indicia indicating applied force value(s), an icon indicating into which range of applied forces the actual applied force falls, or the like. In some embodiments, the device 12 includes an optical element 14 on or proximate a distal tip 30 instead of or in addition to the optical element 14 on the equator 57 of the expandable element 50. In this embodiment, the processing circuitry 72 may compare strain data to reference data and to visualization of the tissue performed by one or more imaging systems to determine whether the applied force and imagery indicates that the device 12 is being pressed against the pulmonary vein ostium and/or antrum (target tissue) or surrounding tissue (non-target tissue), and generates an alert signal to communicate this determination to the user. For example, if the expandable element 50 is properly seated against the pulmonary vein ostium, the distal tip 30 of the device 30 may be located within the pulmonary vein and not in contact with tissue. Therefore, the FBG 36 of the optical element 14 at or on the distal tip 30 may measure minimal or no strain. Conversely, if the expandable element 50 is pressed against the atrial wall, the FBG 36 of the optical element 14 at or on the distal tip 30 may measure strain.

Continuing to refer to FIG. 15, if the processing circuitry 72 determines that the device 12 is being pressed against non-target tissue, the user receives this determination as an alert signal and repositions the device 12 (Step 110). In one embodiment, Steps 1-5 are then repeated until the processing circuitry 72 determines that the device 12 is being pressed against target tissue. In one embodiment, the processing circuitry 72 is configured to provide an alert to the user that the optimal force and/or contact have been achieved prior to initiating ablation of the tissue. The processing circuitry 72 may also be configured to provide safety feedback to the user, such as an alert if excessive force is measured. Further, if full contact and/or occlusion is not possible, it may still be desirable to initiate ablation. In another embodiment, the processing circuitry 72 is configured to automatically prevent a circulation of coolant through the expandable element 50 that would be sufficient to reduce the expandable element 50 to a temperature capable of ablating tissue, which in some cases may avoid unintentional tissue damage and patient injury. For example, the processing circuitry 72 may close one or more valves between a coolant source reservoir 64 and the expandable element 50. Once the processing circuitry 72 determines that the device 12 is being pressed against target tissue, this information is communicated to the user and the processing circuitry 72 automatically or semi-automatically initiates, or the user manually initiates, circulation of coolant through the expandable element 50 sufficient to reduce the expandable element 50 to a temperature capable of ablating tissue (Step 112).

Embodiments

In one embodiment, a medical device 12 comprises: an elongate body 18 including a distal portion 22 and a proximal portion 20 opposite the distal portion 22; and an optical element 14 located at the distal portion 22 of the elongate body 18.

In one aspect of the embodiment, the optical element 14 includes: at least one optical fiber 34 having a distal portion and a proximal portion opposite the distal portion; and a fiber Bragg grating (FBG) 36 located within the distal portion of the optical fiber 34. In one aspect of the embodiment, the medical device 12 is a dilator, wherein the medical device 12 includes a lumen 24 that is sized and configured to receive a puncture element 28. In one aspect of the embodiment, the optical element 14 is integrated with an external surface of the elongate body 18.

In one aspect of the embodiment, at least a portion of the optical element 14 is external to the elongate body 18.

In one aspect of the embodiment, at least a first portion of the optical element 14 is external to the elongate body 18 and at least a second portion of the optical element 14 is within the lumen 24, the at least a first portion including the FBG 36.

In one aspect of the embodiment, the medical device 12 is a cryotreatment device, and the medical device 12 further comprises: an expandable element 50 at the distal portion 22 of the elongate body 18, the expandable element 50 defining a maximum outer diameter 57; and a distal tip 30 that is distal to the expandable element 50.

In one aspect of the embodiment, the optical element 14 is on the maximum outer diameter 57 of the expandable element 50.

In one aspect of the embodiment, the optical element 14 is proximate the distal tip 30.

In one aspect of the embodiment, the optical element 14 is a first optical element, the medical device 12 further comprising a second optical element 14, the first optical element being on the maximum outer diameter 57 of the expandable element 50 and the second optical element being one of on and proximate the distal tip 30.

In one embodiment, a medical system 10 comprises: a medical device 12, the medical device 12 including: an elongate body 18 including a distal portion 22 and a proximal portion 20 opposite the distal portion 22; and an optical element 14 located at the distal portion 22 of the elongate body 18, the optical element 14 including at least one optical fiber 34 having a distal portion and a proximal portion opposite the distal portion and a fiber Bragg grating (FBG) 36 located within the distal portion of the optical fiber 34; a control unit 16 in communication with the medical device 12, the control unit 16 including: an optical interrogator 68 in communication with the optical element 14; and processing circuitry 72 configured to receive data from the optical interrogator 68.

In one aspect of the embodiment, the medical device 12 is configured to thermally affect tissue, the medical device further including a treatment element 50 at the distal portion 22 of the elongate body 18, the optical element 14 being coupled to the treatment element 50. In one aspect of the embodiment, the treatment element 50 is a balloon defining an equator 57, the optical element 14 being on the equator 57 of the expandable element.

In one aspect of the embodiment, the medical device 12 is configured to puncture septal tissue, the medical device further including a lumen 24 extending between the proximal 20 portion and the distal portion 22, at least a first portion of the optical element 14 being external to the elongate body 18 and at least a second portion of the optical element 14 being within the lumen 14, the at least a first portion including the FBG 36.

In one embodiment, a method of quantifying a force exerted by a medical device 12 against an area of tissue comprises: placing a distal portion 22 of a medical device 12 in contact with an area of tissue, the medical device 12 including an optical element 14, the optical element 14 having an optical fiber 34 with fiber Bragg grating 36; advancing the medical device 12 such that the distal portion 22 of the medical device 12 exerts a force against the area of tissue; obtaining strain data from the optical element 14 with an optical interrogator 68; transmitting strain data from the optical interrogator 68 to processing circuitry 72, the processing circuitry 72 correlating the strain data to a pressure value; and repositioning the medical device 12 when the pressure value indicates the distal portion 22 of the medical device 12 is in contact with non-target tissue.

In one aspect of the embodiment, the medical device 12 further includes an elongate body and a puncture element 28 at least partially within the elongate body 18, and the method further comprises: automatically preventing, by the processing circuitry 72, advancement of the puncture element 28 from the elongate body 18 and through the area of tissue when the pressure value indicates the distal portion 22 of the medical device 12 is in contact with non-target tissue.

In one aspect of the embodiment, the medical device 12 is a dilator, wherein the medical device 12 includes a lumen 24 that is sized and configured to receive the puncture element 28. In one aspect of the embodiment, at least a portion of the optical element 14 is integrated with an external surface of the elongate body 18.

In one aspect of the embodiment, the medical device 12 further includes a treatment element 50 configured to cryoablate tissue, and the method further comprises: automatically preventing, by the processing circuitry 72, circulation of a coolant through the treatment element 50 that is configured to lower a temperature of the treatment element to a temperature that is sufficient to cryoablate tissue.

In one aspect of the embodiment, the medical device 12 includes a treatment element 50, the treatment element 50 defining an equator 57, the optical element 14 being on the equator 57 of the treatment element 50, the step of placing a distal portion 22 of the medical device 12 in contact with an area of tissue including placing at least a portion of the equator 57 of the treatment element 50 in contact with an area of tissue.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system comprising:
   a medical device, the medical device including:
   an elongate body including a distal portion and a proximal portion opposite the distal portion; and
   an optical element located at the distal portion of the elongate body, the optical element including at least one optical fiber having a distal portion and a proximal portion opposite the distal portion and a fiber Bragg grating (FBG) located within the distal portion of the optical fiber, the optical element configured to provide an output indicative of a linear force exerted on an area of tissue by the elongate body based on spacing of the FBG;
   a control unit in communication with the medical device, the control unit including:
   an optical interrogator in communication with the optical element, the optical interrogator configured to receive the output from the optical element; and
   processing circuitry configured to:
   receive data from the optical interrogator;
   determine the linear force exerted on the area of tissue based on the output;
   compare the determined linear force exerted on the area of tissue to an image of the area of tissue performed by an imaging system in communication with the processing circuitry;
   determine whether the distal portion of the elongate body is in contact with non-target tissue based on the comparison;
   generate an alert to a display when the processing circuitry determines that the distal portion of the elongate body is in contact with non-target tissue; and
   automatically prevent an operation of the medical device on the area of tissue when the processing circuitry determines that the distal portion of the elongate body is in contact with non-target tissue.

2. The medical system of claim 1, wherein the medical device is a dilator, wherein the medical device includes a lumen that is sized and configured to receive a puncture element.

3. The medical system of claim 2, wherein the optical element is integrated with an external surface of the elongate body.

4. The medical system of claim 3, wherein at least a portion of the optical element is external to the elongate body.

5. The medical system of claim 3, wherein at least a first portion of the optical element is external to the elongate body and at least a second portion of the optical element is within the lumen, the at least a first portion including the FBG.

6. The medical system of claim 1, wherein the medical device is a cryotreatment device, the medical device further comprising:
   an expandable element at the distal portion of the elongate body, the expandable element defining a maximum outer diameter; and
   a distal tip that is distal to the expandable element.

7. The medical system of claim 6, wherein the optical element is on the maximum outer diameter of the expandable element.

8. The medical system of claim 6, wherein the optical element is proximate the distal tip.

9. The medical system of claim 6, wherein the optical element is a first optical element, the medical device further comprising a second optical element, the first optical element being on the maximum outer diameter of the expandable element and the second optical element being one of on and proximate the distal tip.

10. The medical system of claim 1, wherein the medical device is configured to thermally affect tissue, the medical device further including a treatment element at the distal portion of the elongate body, the optical element being coupled to the treatment element.

11. The medical device of claim 10, wherein the treatment element is a balloon defining an equator, the optical element being on the equator of the expandable element.

12. The medical device of claim 1, wherein the medical device is configured to puncture septal tissue, the medical device further including a lumen extending between the proximal portion and the distal portion, at least a first portion of the optical element being external to the elongate body and at least a second portion of the optical element being within the lumen, the at least a first portion including the FBG.

* * * * *